(12) United States Patent
Seth

(10) Patent No.: US 6,531,153 B2
(45) Date of Patent: Mar. 11, 2003

(54) COMPOSITION WITH SUSTAINED RELEASE OF LEVODOPA AND CARBIDOPA

(75) Inventor: Pawan Seth, Irvine, CA (US)

(73) Assignee: Drugtech Corporation, Wilmington, DE (US)

(*) Notice: Subject to any disclaimer, the term of this patent is extended or adjusted under 35 U.S.C. 154(b) by 0 days.

(21) Appl. No.: 09/866,857

(22) Filed: May 29, 2001

(65) Prior Publication Data

US 2002/0192290 A1 Dec. 19, 2002

(51) Int. Cl.[7] ................................................. A61K 9/14
(52) U.S. Cl. ..................... 424/486; 424/489; 424/488
(58) Field of Search ..................... 424/486, 473, 424/488, 78.36, 489; 514/567, 649, 654

(56) References Cited

U.S. PATENT DOCUMENTS

| | | | |
|---|---|---|---|
| 4,424,235 A | | 1/1984 | Sheth et al. |
| 5,190,763 A | * | 3/1993 | Edgren et al. ............... 424/473 |
| 5,525,631 A | * | 6/1996 | Milman et al. .............. 514/567 |
| 5,532,274 A | | 7/1996 | Wenzel et al. |

FOREIGN PATENT DOCUMENTS

| | | | |
|---|---|---|---|
| EP | 0 253 490 | * | 1/1998 |
| WO | WO 99/04765 | | 2/1999 |

* cited by examiner

Primary Examiner—Thurman K. Page
Assistant Examiner—Blessing Fubara
(74) Attorney, Agent, or Firm—Nath & Associates PLLC; Gary M. Nath

(57) ABSTRACT

The invention relates to a pharmaceutical composition comprising a therapeutically effective amount of levodopa and of carbidopa, dispersed in a hydrophilic matrix, said composition further comprising an organic acid. A subject of the invention is also a process for preparing the composition, comprising granulation, in particular in a fluidized bed, of the various components and compression of the granules obtained.

12 Claims, 1 Drawing Sheet

COMPOSITION WITH SUSTAINED RELEASE OF LEVODOPA AND CARBIDOPA

SUBJECT AND SUMMARY OF THE INVENTION

The present invention consists of a formulation with sustained release of a combination of two active principles, namely levodopa and carbidopa.

PRIOR ART

In the case of two combined active principles, it is desirable, for certain dosage forms, for them to have:

an extended release of the two active principles over a period of several hours, and with identical release profiles for the two substances;

a stability of the formulation over time, for example over a period of at least 6 months under accelerated conditions as described in the European and American pharmacopoeias.

This is particularly true for levodopa and carbidopa combinations. Specifically, carbidopa is a relatively fragile molecule and formulations containing this product often show relatively poor conservation, particularly at high temperature and high humidity.

Various formulations corresponding to a levodopa/carbidopa combination with sustained release are disclosed in the literature.

Document U.S. Pat. No. 5 840 756 discloses a matrix based on hydroxypropylmethylcellulose, hydroxypropylcellulose an a carboxyvinyl polymer and containing different proportions of levodopa and carbidopa. This formulation is obtained by direct compression of the mixture of the constituents. The drawback of such a process lies in the difficulty in obtaining a uniform distribution of the active principles during direct compression. This formulation does not have good stability.

Document EP-A-0 253 490 discloses a formulation of levodopa and carbidopa uniformly dispersed in a polymeric matrix consisting of a mixture of two polymers, one of which is water-soluble, such as hydroxypropyl(methyl)cellulose, and the other of which is weakly soluble, such as polyvinyl acetate/crotonic acid copolymer. Such a formulation is, firstly, complex (it requires the steps of mixing the active compounds with an aqueous-alcoholic solution of the polymers, drying, grinding, mixing with the lubricant and finally compressing into tablets), and secondly there is no indication as to the stability of the preparation.

No formulation of the prior art makes it possible simultaneously to obtain a parallel sustained release of the two principles with high stability over time, while at the same time being simple in its composition and implementation.

SUMMARY OF THE INVENTION

The invention relates to a pharmaceutical composition comprising a therapeutically effective amount of levodopa and of carbidopa, dispersed in a hydrophilic matrix, said composition further comprising an organic acid.

According to one embodiment, the organic acid is chosen from fumaric acid, citric acid, ascorbic acid, maleic acid, glutamic acid, malonic acid and oxalic acid.

According to one embodiment, the organic acid represents from 0.2% to 5% by weight relative to the weight of the composition.

According to one embodiment, the hydrophilic matrix represents from 10% to 80% by weight relative to the weight of the composition.

According to one embodiment, the hydrophilic matrix comprises hydroxypropylmethylcellulose.

According to one embodiment, the hydrophilic matrix comprises, as a percentage by weight relative to the weight of the composition, between 5% and 40% of hydroxypropylmethylcellulose with a viscosity of about 50 cP and between 5% and 40% by weight of hydroxypropylmethylcellulose with a viscosity of about 3 cP.

According to one embodiment, the hydrophilic matrix moreover comprises an insoluble substance.

According to one embodiment, the insoluble substance is microcrystalline cellulose.

According to one embodiment, the levodopa is present in an amount of between 50 mg and 300 mg.

According to one embodiment, the carbidopa is present in an amount of between 10 mg and 80 mg.

According to one embodiment, the composition is in the form of granules compressed together.

The composition according to the invention is useful in the treatment of Parkinson's disease.

The invention also relates to a process for preparing a composition according to the invention, comprising granulation of the various components and compression of the granules obtained.

According to one embodiment, the granulation is carried out in a fluidized bed.

DESCRIPTION OF THE INVENTION

Figure 1:
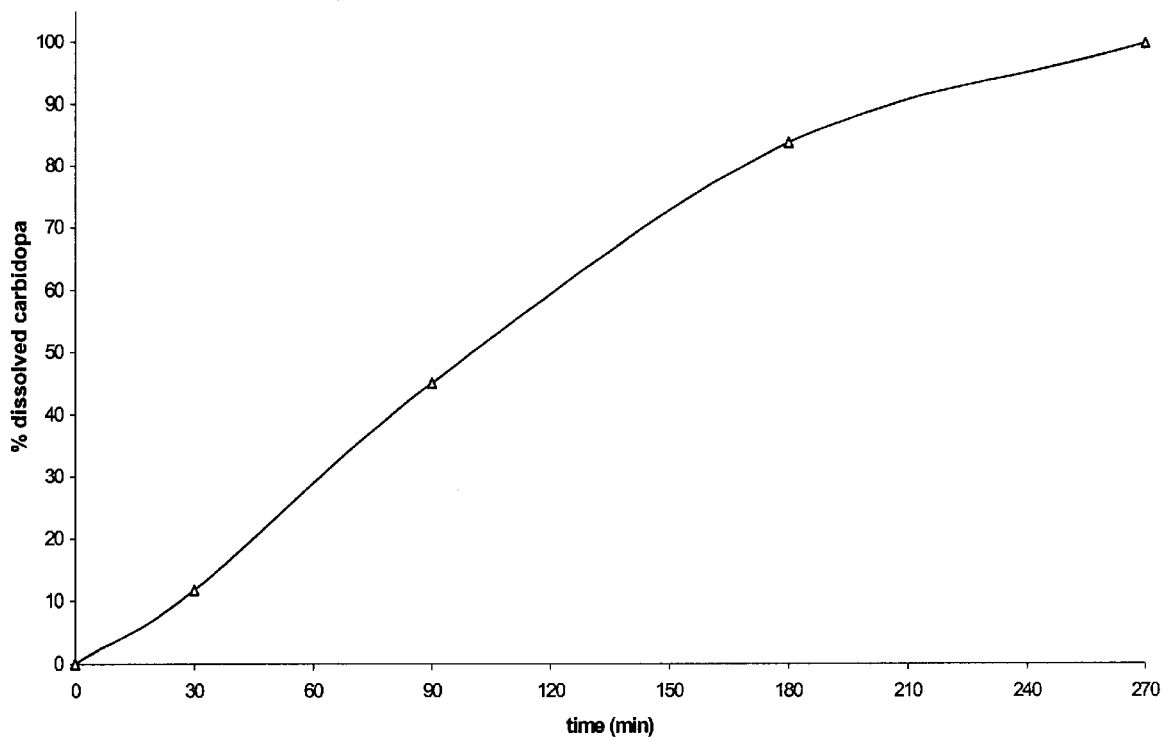
FIG. 1 represents the dissolution as a function of time of the composition of Example 1.

The composition according to the invention comprises, in addition to the active principles, a hydrophilic matrix and an organic acid.

The Applicant has discovered, surprisingly, that the chemical stability of carbidopa can be greatly improved by incorporating into the formulation a small amount of an organic acid. This organic acid is typically a weak organic acid such as fumaric acid. Many other weak organic acids may be used to prevent the degradation of carbidopa, such as, for example, citric acid, maleic acid, tartaric acid, ascorbic acid or glutamic acid.

The hydrophilic matrix generally comprises a gelling substance such as hydroxypropylmethylcellulose. Other gelling components may be used, such as polyvinylpyrrolidone, poly(vinyl alcohol), hydroxypropylcellulose, hydroxymethylcellulose or gelatin, alone or as a mixture.

Mixtures of two different grades of hydroxypropylmethylcellulose, in particular of different viscosities (the viscosity is measured at 2% and at 20° C.), are suitable.

The hydrophilic matrix may also comprise a substance, in general an insoluble substance such as microcrystalline cellulose. Other insoluble compounds may be used.

The amount of this insoluble substance present is generally in an insoluble substance:gelling substance weight ratio of between 15:100 and 50:100 and preferably 1:3.

Other conventional excipients may be used.

The invention is generally in the form of a tablet. This tablet is obtained in particular by compressing granules. These granules are advantageously obtained by granulating the constituent principles, for example according to a process in a fluidized air bed, followed by compression.

This process of granulation in a fluidized bed is conventional and known to those skilled in the art. According to the conventional art, a powder or a mixture of powders (active principles+excipients) is placed in suspension in the form of a fluidized bed in a granulator, and a solution containing a binder and, optionally, a surfactant is sprayed onto this bed to form granules. This technique of granulation in a fluidized bed is disclosed in particular in, for example, "Die Tablette", by Ritschel, Ed. Cantor Aulendorf, pages 211–212.

The granulate obtained is then mixed with a lubricant present in a proportion generally of between 0.1% and 5% by weight, such as, for example, magnesium stearate, sodium stearylfumarate, glyceryl behenate or any other lubricant known to those skilled in the art and disclosed, for example, in Banker GS, Rhodes CT: Modern Pharmaceutics (1996) ISBN 0-8247-9371-4. In order to improve the flow of the mixture on the press, a flow regulator may also be added to the formulation, in a proportion generally of between 0.1% and 4% by weight. Such a substance may be, for example, talc, modified or unmodified starch, or, preferably, colloidal silica such as Aerosil® 200 manufactured by Degussa.

The conventional techniques of direct compression used in the prior art may also be used, although these are less preferred.

The tablets thus obtained are useful for treating Parkinson's disease. They also offer the advantage of avoiding the phenomena of "wearing-off and on-off" conventionally associated with standard formulations of levodopa and carbidopa, such as Sinemet® std.

The term "about" as used in the application means ±10% of the value.

The examples which follow illustrate the invention without limiting it.

EXAMPLES

Example 1

Granules are prepared from the following composition:

| | |
|---|---|
| Levodopa | 200.0 mg |
| Carbidopa (hydrate) | 53.5 mg |
| Hydroxypropylmethylcellulose 50 cP | 60.0 mg |
| Hydroxypropylmethylcellulose 3 cP | 90.0 mg |
| Microcrystalline cellulose | 50.0 mg |
| Polyvinylpyrrolidone K30 | 15.0 mg |
| Fumaric acid | 2.0 mg |

The levodopa, the carbidopa, the microcrystalline cellulose and the two grades of hydroxypropylmethylcellulose are mixed together and placed in a fluidized air bed (GPCG1, Glatt®). A solution of polyvinylpyrrolidone in water is prepared and the fumaric acid is suspended in this solution. To do this, it is convenient to use a fumaric acid of micronized grade. The resulting suspension is sprayed onto the powder mixture at a pumping rate of 15 g/min, an inlet air temperature of about 55° C. and a fluidized-air flow rate of 70 m$^3$/h. A granulate is thus obtained.

The granulate obtained is mixed with 1 % by weight of sodium stearylfumarate and 0.5% by weight of colloidal silica (Aerosil 200). The mixture is compressed on a Fette P2100 rotary press equipped with punches with a diameter of 11 mm and a radius of curvature of 11 mm, to a mass of 415 mg and a hardness of 90 N. A rigorously identical formulation, but without fumaric acid, is then prepared and compressed to a mass of 413 mg.

Study of the Degradation of Carbidopa
Action of Temperature on the Formulation

A tablet of each of the formulations is placed in a graduated flask containing 50 ml of purified water and the mixture is stirred until the active principles have completely dissolved, and placed in an oven at 50° C. for 72 hours. The carbidopa concentration in each of the two solutions is determined by high performance liquid chromatography according to the following method:

Operating Conditions:

Mobile phase: 5% ethanol

95% monobasic sodium phosphate monohydrate (5.2 g/l)

pH adjusted to 2.7 with orthophosphoric acid

Column: NUCLEOSIL C18 5µ250×4.6 mm

Detection: 280 nm

Flow rate: 1.2 ml/min

Volume injected: 20 µ

Retention time: Levodopa: 3.2 min

Fumaric acid: 3.9 min

Carbidopa: 5.5 min

Diluent: 20% 1M H$_3$PO$_4$ and 80% mobile phase

Preparation of the Standard Solution:

Introduce accurately weighed amounts of about 200 mg of reference levodopa and 53.5 mg of reference carbidopa into a 100 ml graduated flask. Dissolve with 20 ml of H$_3$PO$_4$ in an ultrasonic bath for 5 minutes. Cool the solution to room temperature and make up to the graduation mark with the mobile phase. Take 10 ml of the solution and make up to 25 ml with the mobile phase. Filter a few ml of the suspension through a filter (0.45 µm).

The concentrations thus obtained are about:

Levodopa: 0.8 mg/ml

Carbidopa: 0.214 mg/ml

Preparation of the Sample Solution:

Introduce an accurately weighed amount of powder obtained from ground tablets corresponding theoretically to about 200 mg of levodopa and to about 53.5 mg of carbidopa into a 100 ml graduated flask. Dissolve with 20 ml of H$_3$PO$_4$ in an ultrasonic bath for 10 minutes. Cool the solution to room temperature and make up to the graduation mark with the mobile phase (if necessary, wet the neck of the flask with ethanol to eliminate the foam). Take 10 ml of the solution and make up to 25 ml with the mobile phase. Filter a few ml of the suspension through a filter (0.45 µm).

Calculating the results:

The amount Q1, expressed as % of levodopa, is given by the following formula:

$$Q1 = (Asam/Aref) \times (Wref/Wsam) \times (Vd\ sam/Vd\ ref) \times (Wth/C) \times 100$$

where Asam=Area of the peak for the sample solution

Aref=Area of the peak for the reference solution

Wref=Weight of the reference levodopa

Wsam=Weight of the sample

Vd sam=Dilution factor for the sample

Vd ref=Dilution factor for the reference

Wth=Theoretical weight of the tablet

C=Levodopa content of the tablet

The amount Qc, expressed as % of carbidopa, is given by the following formula:

$$Qc = (Asam/Aref) \times (Wref/Wsam) \times (Vd\ sam/Vd\ ref) \times (Wth/C) \times 100$$

where Asam=Area of the peak for the sample solution

Aref=Area of the peak for the reference solution

Wref=Weight of the reference carbidopa

Wsam=Weight of the sample

Vd sam=Dilution factor for the sample

Vd ref=Dilution factor for the reference

Wth=Theoretical weight of the tablet
C=Carbidopa content of the tablet
Results

|  | Formulation with fumaric acid | Control formulation |
|---|---|---|
| Carbidopa (% of the initial value) | 69.2 | 29.5 |

A very marked protective effect of fumaric acid on the degradation of carbidopa is noted.

Action of Light on the Formulation

A tablet of each of the formulations is placed in a graduated flask containing 50 ml of purified water and the mixture is stirred until the active principles have completely dissolved, and exposed to the ambient laboratory light for 72 hours. The carbidopa concentration in each of the two solutions is determined by high performance liquid chromatography according to the following method:

Results

|  | Formulation with fumaric acid | Control formulation |
|---|---|---|
| Carbidopa (% of the initial value) | 96.7 | 66.8 |

The light-stability of carbidopa is also considerably improved by the invention.

The release of active principle by the above formulation is studied according to the method described in the edition of the US pharmacopoeia in force and with the following parameters:

Dissolution medium: 0.1M pH 2.0 citrate buffer
Volume: 1000 ml
Wavelength: 280 nm
Dissolution tool: 40 mesh basket
Stirring speed: 100 rpm HPLC Assay to Separate the Active Principles The dissolution curve is given in FIG. 1.

The dissolution profile obtained shows a sustained release of the active principle over about 5 hours.

Example 2

The above example is repeated, but replacing the fumaric acid with ascorbic acid (these acids are used in the same amounts). The formulation used is as follows:

| Levodopa | 200.0 mg |
|---|---|
| Carbidopa (hydrate) | 53.5 mg |
| Hydroxypropylmethylcellulose 50 cP | 80.0 mg |
| Hydroxypropylmethylcellulose 3 cP | 70.0 mg |
| Microcrystalline cellulose | 50.0 mg |
| Polyvinylpyrrolidone K30 | 15.0 mg |
| Ascorbic acid | 2.0 mg |

The stability of the carbidopa in the above two formulations is studied according to the protocol described previously, with exposure to heat or to light.

Results

Action of heat (50° C. for 72 hours)

|  | Formulation with ascorbic acid | Control formulation |
|---|---|---|
| Carbidopa (% of the initial value) | 58.6 | 29.5 |

Action of light (ambient laboratory light for 72 hours)

|  | Formulation with ascorbic acid | Control formulation |
|---|---|---|
| Carbidopa (% of the initial value) | 94.3 | 66.8 |

The stability is still improved with ascorbic acid (although in a slightly lower proportion relative to the formulation containing fumaric acid).

The release of the active principles shows a profile similar to that of the preceding formulation (although slightly slower, possibly on account of the presence of a larger amount of microcrystalline cellulose).

Example 3

A tablet having the following composition is prepared:

| Levodopa | 200.00 mg |
|---|---|
| Carbidopa (hydrate) | 53.50 mg |
| Hydroxypropylmethylcellulose 50 cP | 50.00 mg |
| Hydroxypropylmethylcellulose 3 cP | 50.00 mg |
| Colloidal silicon dioxide | 2.40 mg |
| Fumaric acid | 10.00 mg |
| FD&C yellow 10 | 0.03 mg |
| FD&C red 3 | 0.03 mg |
| Sodium stearyl fumarate | 7.30 mg |

A 300mg water solution is prepared by dissolving the hydroxypropylmethylcellulose 3cP grade. The dyes are dissolved in 100 mg of water and the micronised fumaric acid is suspended in the solution. These two solutions are then mixed together. The levodopa, the carbidopa, the colloidal silicon dioxide and the hydroxypropylmethylcellulose 50 cP grade are mixed together and placed in a fluidized air bed (GPCG1, Glatt®). The previously prepared solution is sprayed onto the powder mixture at a pumping rate of 15 g/min, an inlet air temperature of about 55° C. and a fluidized-air flow rate of 70 m$^3$/h. A granulate is thus obtained.

The granulate obtained is mixed with the sodium stearylfumarate. The mixture is compressed on a Fette P2100 rotary press as previously disclosed.

Example 4

Example 3 is repeated, but with the following composition:

| Levodopa | 200.00 mg |
| Carbidopa (hydrate) | 53.50 mg |
| Hydroxypropylmethylcellulose 50 cP | 35.00 mg |
| Hydroxypropylmethylcellulose 3 cP | 50.00 mg |
| Colloidal silicon dioxide | 2.40 mg |
| Fumaric acid | 10.00 mg |
| FD&C yellow 10 | 0.03 mg |
| FD&C red 3 | 0.03 mg |
| Sodium stearyl fumarate | 7.00 mg |

Both example 3 and example 4 compositions exhibit improved stability and sustained release.

What is claimed is:

1. Pharmaceutical composition comprising a therapeutically effective amount of levodopa and of carbidopa, dispersed in a hydrophilic matrix, said composition further comprising an organic acid, where this acid is selected from the group consisting of fumaric acid, citric acid, ascorbic acid, maleic acid, glutamic acid, malonic acid and oxalic acid and represents from 0.2% to 5% by weight relative to the weight of the composition, and where the hydrophilic matrix represents from 10% to 80% by weight relative to the weight of the composition, said hydrophilic matrix comprising as a percentage by weight relative to the weight of the composition, between 5% and 40% of hydroxypropylmethylcellulose with a viscosity of about 50 cP and between 5% and 40% by weight of hydroxypropylmethylcellulose with a viscosity of about 3 cP.

2. Composition according to claim 1, in which the levodopa is present in an amount of between 50 mg and 300 mg and the carbidopa is present in an amount of between 10 mg and 80 mg.

3. Composition according to claim 1, in the form of granules compressed together.

4. A method for treating Parkinson's disease, comprising administering a composition according to claim 1.

5. A process for preparing a pharmaceutical composition comprising a therapeutically effective amount of levodopa and of carbidopa, dispersed in a hydrophilic matrix, said composition further comprising an organic acid wherein the hydrophilic matrix represents 10% to 80% by weight of the composition, comprising:
   (a) mixing a therapeutically effective amount of levodopa and of carbidopa with a hydrophilic matrix comprising a gelling substance;
   (b) granulating the various components of step (a); and
   (c) compressing the granules obtained from step (b).

6. A process according to claim 5, in which the granulating step is carried out in a fluidized bed.

7. A process for preparing a pharmaceutical composition comprising a therapeutically effective amount of levodopa and of carbidopa, dispersed in a hydrophilic matrix, said composition further comprising an organic acid, where the acid is selected from the group consisting of fumaric acid, citric acid, ascorbic acid, maleic acid, glutamic acid, malonic acid, and oxalic acid and represents from 0.2% to 5% by weight relative to the weight of the composition, comprising:
   (a) mixing a therapeutically effective amount of levodopa and of carbidopa with a hydrophilic matrix comprising a gelling substance;
   (b) granulating the various components of step (a); and
   (c) compressing the granules obtained from step (b).

8. A process according to claim 7, in which the granulating step is carried out in a fluidized bed.

9. A process for preparing a pharmaceutical composition comprising a therapeutically effective amount of levodopa and of carbidopa, dispersed in a hydrophilic matrix, said composition further comprising an organic acid, where the acid is selected from the group consisting of fumaric acid, citric acid, ascorbic acid, maleic acid, glutamic acid, malonic acid, and oxalic acid and represents from 0.2% to 5% by weight relative to the weight of the composition, and where the hydrophilic matrix represents from 10% to 80% by weight relative to the weight of the composition, said hydrophilic matrix comprising as a percentage by weight relative to the weight of the composition, between 5% and 40% of hydroxypropylmethylcellulose with a viscosity of about 50 cP and between 5% and 40% by weight of hydroxypropylmethylcellulose with a viscosity of about 3 cP, comprising:
   (a) mixing a therapeutically effective amount of levodopa and of carbidopa with a hydrophilic matrix;
   (b) granulating the various components of step (a); and
   (c) compressing the granules obtained from step (b).

10. A process according to claim 9, in which the granulating step is carried out in a fluidized bed.

11. A composition according to claim 5, wherein the gelling substance is selected from the group consisting of hydroxypropylmethylcellulose, polyvinylpyrrolidone, poly(vinyl alcohol), hydroxypropylcellulose, hydroxymethylcellulose, gelatin, and combinations thereof.

12. A composition according to claim 8, wherein the gelling substance is selected from the group consisting of hydroxypropylmethylcellulose, polyvinylpyrrolidone, poly(vinyl alcohol), hydroxypropylcellulose, hydroxymethylcellulose, gelatin, and combinations thereof.

* * * * *